United States Patent [19]

Kozam et al.

[11] Patent Number: 4,512,769
[45] Date of Patent: Apr. 23, 1985

[54] PATIENT EMPLOYED DIGITAL OPERATED SYRINGE DEVICE FOR IRRIGATING PERIODONTAL POCKETS AND OTHER SOFT TISSUE SPACES

[76] Inventors: George Kozam, 234 E. Clinton Ave., Tenafly, N.J. 07670; Pat Romanelli, 224 Brook St., Harrington Park, N.J. 07640

[21] Appl. No.: 510,986

[22] Filed: Jul. 5, 1983

[51] Int. Cl.$^3$ .............................................. A61M 5/00
[52] U.S. Cl. ................................. 604/209; 604/264; 433/80
[58] Field of Search ............... 604/209, 208, 264, 275, 604/30, 36, 38, 39, 21; 433/80

[56] References Cited

U.S. PATENT DOCUMENTS

| | | | |
|---|---|---|---|
| 201,443 | 3/1878 | Parker | 604/209 |
| 1,586,302 | 5/1926 | Funk | 433/80 |
| 3,199,510 | 8/1965 | Sinai | 604/275 X |
| 3,977,574 | 8/1976 | Thomas | 604/209 |
| 4,276,880 | 7/1981 | Malmin | 604/264 |

Primary Examiner—John D. Yasko
Attorney, Agent, or Firm—Edward F. Levy

[57] ABSTRACT

A periodontal lavage syringe is provided for self home use by an unskilled patient in the treatment of periodontal disease by irrigation of periodontal pockets or other soft tissue spaces. The syringe may have a single liquid retaining barrel or preferably multiple barrels, each of which contains a dispensible plunger and each of which is filled with a different treatment fluid. The bores communicate with a single liquid outlet to which is attached a flexible needle or tube terminating in a nozzle which is preferably elastomeric. The nozzle is conical in shape, having a pointed tip which enables easy insertion of the nozzle into the periodontal pocket, and tapered walls, the increasing diameter of which limits the depth of insertion of the nozzle within the pocket. Ratchet devices mounted on the syringe body are coupled to the plungers and are manually operable by the fingers of the user's hand holding the syringe to feed the different liquids successively and alternately into the periodontal pocket in equal pre-selected incremental doses.

9 Claims, 4 Drawing Figures

FIG. 2
FIG. 1
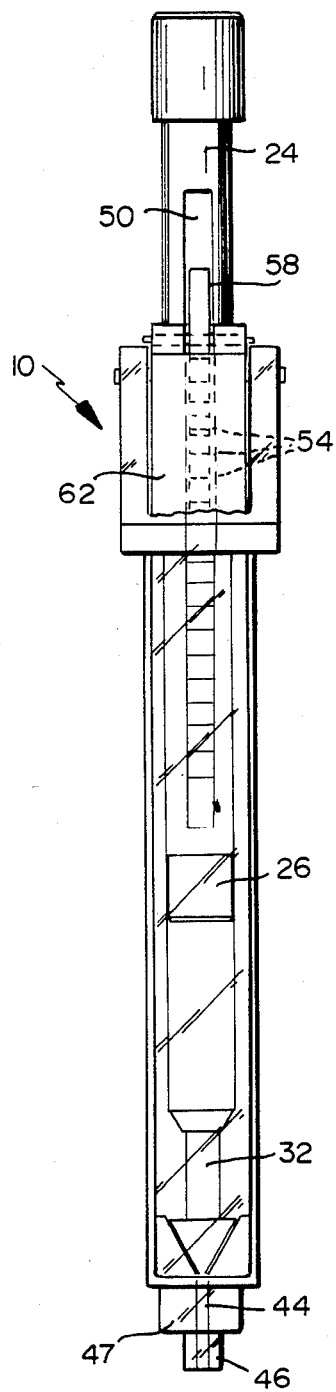
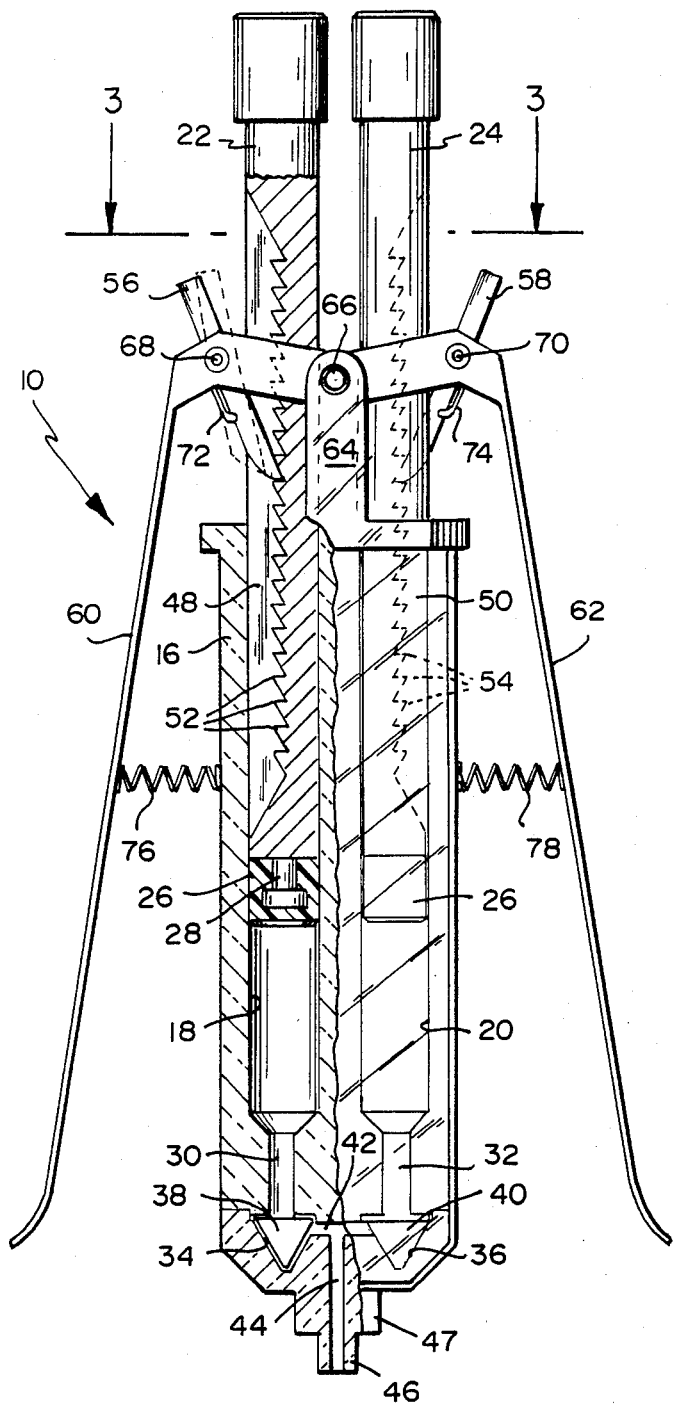

PATIENT EMPLOYED DIGITAL OPERATED SYRINGE DEVICE FOR IRRIGATING PERIODONTAL POCKETS AND OTHER SOFT TISSUE SPACES

BACKGROUND OF THE INVENTION

The periodontal disease known as pyorrhea is caused by the accumulation of bacteria, food debris and pus, i.e. placque, in the crevice between the gum margin and the tooth. When hygienic conditions are lacking, the bacterial toxins which are produced induce inflammation of the gingiva, resulting in deepening of the crevice and the creation of a pocket. This space, which is hidden from the normal tooth brushing and lavage, permits bacteria to multiply rapidly causing the pocket to deepen further. The gum margin, inflamed from the persistent bacterial toxins produced in the vicinity, begins to swell, causing pain and also causing the body structure of the tooth socket to dissolve, resulting in increased mobility of the tooth and its eventual loss.

Periodontal disease is a widespread affliction, and it is conventionally treated by a dentist who manually scrapes out the accumulated material between the gum and the teeth and may also irrigate the periodontal pockets which exist. Such procedure requires frequent visits by the patient to the dentist since the treatment requires specialized techniques and apparatus. There are no devices presently available by means of which a patient may effectively treat a periodontal condition by self-administration.

It is an object of the present invention to provide a device for the cleansing of gingival pockets which may be kept and used at home by any person suffering from periodontal disease, and which in operation is effective as a periodontal lavage syringe to place antiseptic and other medicinal irrigants in the circumscribed areas which are inaccessible to the lavage and brushing conventionally done by the patient or that occur naturally by the flow of saliva.

Another object of the invention is the provision of a periodontal lavage syringe of the character described in which the treatment fluids are contained within the syringe itself so that the device does not require connection to high pressure water sources or other external equipment. The syringe is therefore light and sufficiently portable that it may be carried in the pocket so that the periodontal patient may conveniently carry it to work or on trips in order to promote and maintain hygienic gingival conditions throughout the day.

Another object of the invention is to provide a periodontal lavage syringe of the character described which has a flexible nozzle sized and shaped to enter gingival pockets easily and painlessly and to deposit small amounts of solutions which remove food particle debris, bacterial clumps and pus by physical lavage, and in addition may also contain agents which induce antisepsis, sedation, and prevent placque from adhering to the surface of the tooth. This method of hygiene promotion thus acts to prevent periodontal disease by preventing placque formation and plaque adhesion, or to control such conditions if they have already started. While the main purpose of the syringe device is to enter and irrigate deep periodontal pockets, it may also be used effectively to dislodge food particles and bacteria in the embrasures between teeth.

A further object of the invention is the provision of a periodonal lavage syringe of the character described which is designed for simple and convenient one-handed operation by a layman unskilled in dentistry or dental techniques. A lever and ratchet arrangement enables the user to dispense small measured amounts of one or more treatment fluids in successive increments, thereby preventing the discharge of large doses of the fluids which would cause pain or inflammation in the sensitive pocket area.

SUMMARY OF THE INVENTION

In accordance with the invention, there is provided a periodontal lavage syringe adapted to provide a safe and effective method of irrigating periodontal pockets and defects as well as other soft tissue spaces by the user who is an unskilled layman. The syringe has a body portion containing at least one fluid-retaining bore and fluid conduit means connecting the bore to a fluid outlet coupling mounting an elongated flexible needle terminating in a conical nozzle having a pointed tip, tapered side walls progressively increasing in diameter from the tip to the opposite end of the nozzle, and an internal longitudinal bore communicating with the interior of said needle. The nozzle also has at least one outlet opening communicating with said longitudinal bore and a plurality of spaced reflux grooves in the surface of said nozzle extending from said outlet opening to the upper portion of said nozzle. The syringe body mounts manually operable ratchet means operatively coupled to the plunger for depression thereof in selected calibrated increments upon manual actuation of the ratchet means by a digit of the hand of the user holding the syringe body portion.

In a preferred embodiment the syringe is a multiple barrel syringe having a plurality of liquid retaining bores, specifically two bores. Each of these bores contains an individual plunger and each plunger is associated with an individual ratchet means for selective actuation by one hand of the user. Each bore contains a different treatment fluid which may be dispensed alternately and selectively by the user into the periodontal pocket within which the nozzle is inserted.

The nozzle may be made of an elastomeric material and is sized for insertion into a periodontal pocket in the mouth of the user, the pointed tip of the nozzle enabling easy insertion of the nozzle into the pocket, and the increasing diameter of the nozzle provided by the tapered walls limiting the depth to which the nozzle can be inserted and preventing the pointed tip from contacting the bottom wall of the pocket. The outlet openings of the nozzle are located above the pointed tip and are positioned to direct the stream of ejected fluid laterally from the nozzle rather than longitudinally.

Additional objects and advantages of the invention will become apparent during the course of the following specification when taken in connection with the accompanying drawings, in which:

BRIEF DESCRIPTION OF THE DRAWINGS

FIG. 1 is a side elevational view of a syringe device made in accordance with the present invention, the syringe being shown partially in section to reveal inner constructional details;

FIG. 2 is an end elevational view of the syringe shown in FIG. 1;

DESCRIPTION OF THE PREFERRED EMBODIMENT

Figure 3:
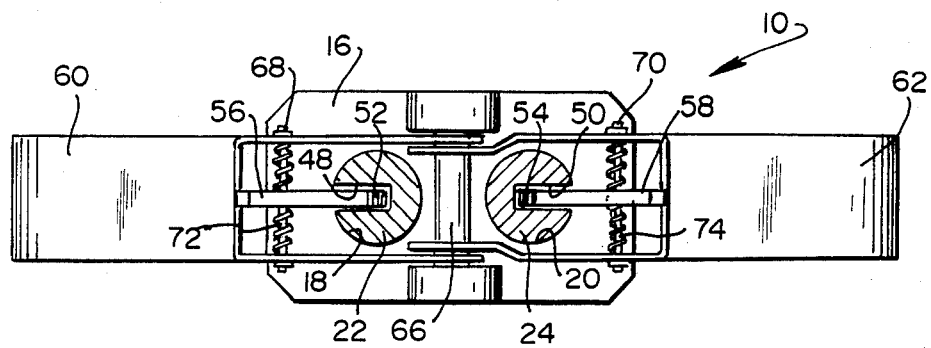
FIG. 3 is top plan view of the syringe of FIG. 1, with portions of the plungers broken away and shown in section, as taken along line 3—3 of FIG. 1.

Referring in detail to the drawings, there is shown in FIG. 1 a syringe device 10 made in accordance with the present invention, and constituting with a universal rotating adapter 12 mounting a nozzle 14 (FIG. 4), a syringe assembly for irrigating periodontal pockets and defects.

The syringe 10 has a body 16 made of a rigid material such as metal, plastic or glass, the body being formed with dual spaced bores 18 and 20, each of which contains a respective slidable plunger 22,24. The syringe, in its preferred embodiment, is therefore a multiple barrel syringe for dispensing a plurality of different fluids, although the invention may also be employed with a single barrel syringe, as will be presently explained. Each plunger 22 and 24 terminates in an elastomeric stopper 26 mounted on a stud 28, the stopper 26 providing a fluid-tight seal with the wall of its respective bore.

At their lower ends, the bores 18 and 20 terminate in respective conduits 30 and 32 of reduced diameter for the transmission of fluids from said bores in response to depression of the respective plungers 22 and 24 in said bores. The conduits 30 and 32 extend to and open into respective cone-shaped recesses 34 and 36 which house one-way valves 38 and 40. Each of the valve recesses 34 and 36 communicate, via a common cross-channel 42, with a Luhr lock bore 44 which extends through a conventional Luhr 46.

Each of the one-way check valves 38 and 40 is made in the form of a solid, cone-shaped membrane or cup being made of a flexible and deformable material such as rubber, having a shape-retaining memory. The valves 38 and 40 are made of the same size and shape as the interior of the valve recesses 34 and 36, so that they fit snugly within the latter and normally fill the interior of the valve recesses, as shown in FIGS. 1 and 2. When either of the plungers 22 or 24 is depressed to force fluid under pressure through the respective conduit 30 or 32, the underlying valve 38 or 40 will deform, clearing a path for the fluid to the cross-channel 32 and thence to the Luer lock bore 44. On the other hand, the opposite valve is not deformed, and its flat wall covers over the mouth of cross-channel 32, thereby preventing the fluid forced from the first syringe bore from entering the other syringe bore.

At its outer side, each plunger 22,24 is formed with a respective elongated recess 48,50 within which is formed a linear row of ratchet teeth 52,54. Operatively associated with each row of ratchet teeth is a respective pawl 56,58 carried by a lever 60,62. The levers 60 and 62 are both mounted on an upstanding extension 64 of the syringe body 16 by a common pivot 66. The pawls 56 and 58 are mounted on the levers 60,62 by respective pivots 68,70, and springs 72,74 urge the plungers into engagement with the respective ratchet teeth. An additional pair of springs 74 and 76 are provided to urge the levers 60 and 62 to inoperative positions shown in FIG. 1 in which the levers are spaced outwardly of the syringe body 16. The springs 74 and 76 are shown in FIG. 1 as coil springs, although leaf springs may be advantageously employed for the same purpose.

Figure 4:
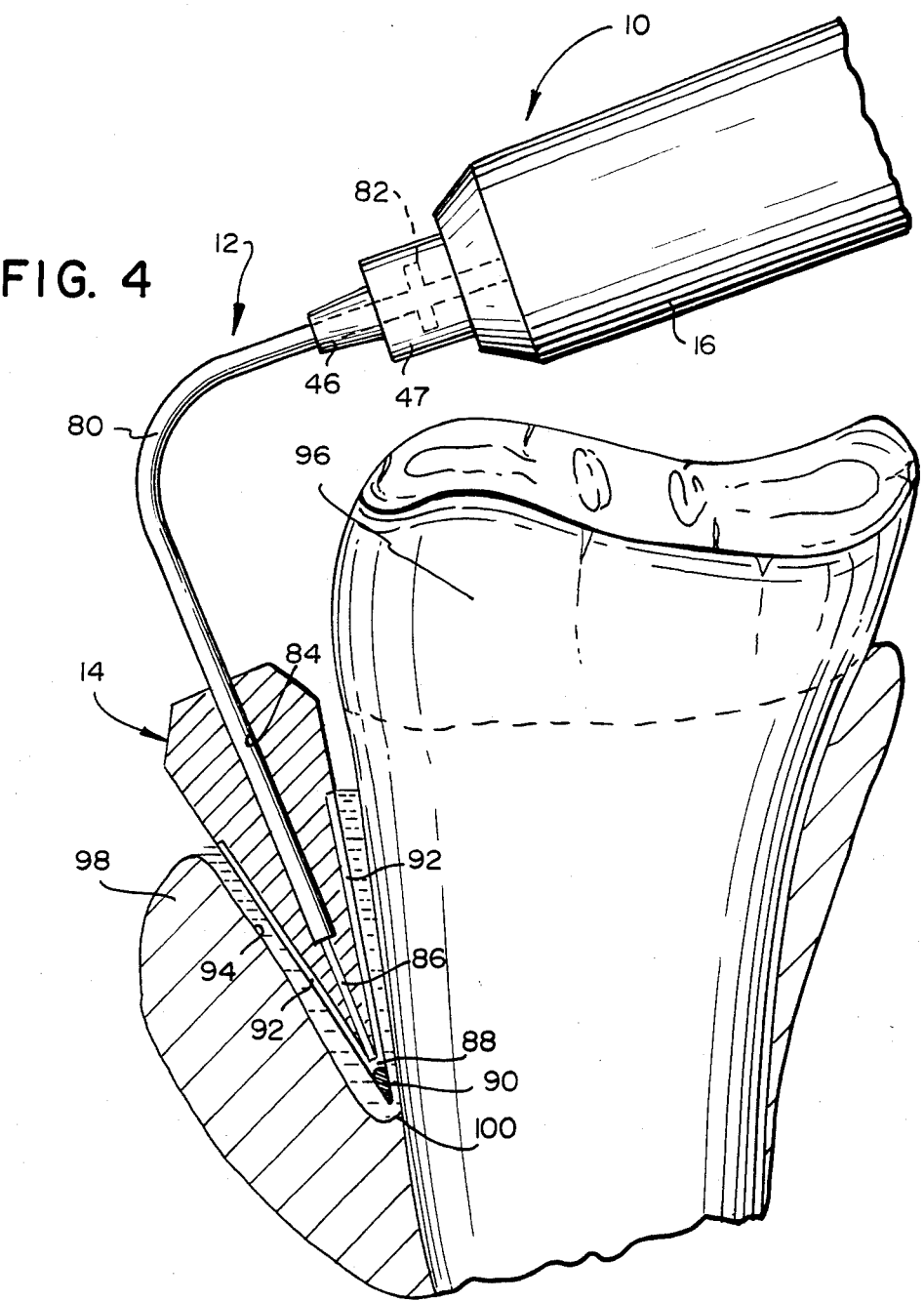
FIG. 4 is a sectional view of the user's mouth showing the syringe device applied to a periodontal pocket between a tooth and the gum.

FIG. 4 shows the adapter 12 and nozzle 14 which are attached to the syringe 10. The adapter comprises an elongated flexible tube or needle 80 affixed to the Luhr 46 which is held in place by a flange 82 securing the Luhr 46 into Luhr lock 47, thereby ensuring a tight and leakproof assembly. At the end of needle 80 is mounted the flexible lavage nozzle 14. Nozzle 14 has an axial bore 84 which which is slightly smaller in diameter than the external diameter of needle 80 so that it is force mounted thereon to provide a tight leakproof fit. Bore 84 communicates with a bore 86 of smaller diameter which terminates in a chamber 88 located close to the tip 90 of the nozzle 14. The chamber 88 in turn communicates with a plurality of spaced reflux grooves 92 which are impressed in the peripheral surface of the nozzle 14. Preferably four of the grooves 92 are provided, these grooves being equally spaced, and all extending longitundinally from a point near the tip 90 to a point above the level of maximum insertion of the nozzle in a periodontal pocket.

The nozzle 14 is of the cone-shaped configuration shown in FIG. 4, and is preferably made of soft rubber or elastomeric plastic material. The conical shape results in the pointed tip 90 which the user can easily insert into the periodontal pocket to be treated. The tapered walls of the nozzle prevent the latter from being inserted too deeply into a periodontal pocket because of the progressively increasing diameter of the nozzle. The pointed tip of the nozzle thus assists the user in finding and entering the pocket and in guiding the nozzle inwardly as far as the progressively increasing diameter will permit. FIG. 4 shows the nozzle 14 inserted into a periodontal pocket 94 between tooth 96 and the surrounding gum 98. The depth of insertion is determined by the limit of tissue elasticity. This prevents over-insertion and protects the cul-de-sac bottom 100 of the pocket 94 from injury.

The nozzle 14 and Luhr 46 may be made separately and secured at opposite ends of a bent steel needle 80, or the adapter 12 may be made entirely of plastic and molded integrally in one piece. In the latter instance, the Luhr 46, made of firm plastic, is formed integrally with a semi-rigid plastic tube 80, the opposite end of which is formed integrally with a pliable plastic nozzle 14.

With the nozzle 14 inserted into the pocket 94 as shown, depression of either lever 60 or 62 will force fluid from the syringe 10 through the needle or tube 80 and through nozzle bore 86 into the chamber 88 from which it is directed radially to the reflux grooves 92 and thence to the side walls of the pocket 94. The fluids are thus discharged laterally from the nozzle rather than longitudinally, thereby protecting the cul-de-sac bottom 100 from a direct stream of irrigant. Under certain conditions the liquid discharge opening may be placed in the tip 90 of the nozzle, although in most cases it is preferred and advantageous to space it above the nozzle tip and to direct the discharge stream in a lateral direction. In the preferred embodiment shown in FIG. 4, the nozzle 14 is ½ cm wide at its maximum diameter and 2 cm in length. The chamber 88 is located 1 mm above the nozzle tip 90.

The grooves 92 prevent binding and seating of the nozzle in the rim of the pocket and also permit a reflux of excess fluid to the exterior of the pocket, thus preventing excessive pressure build-up within the pocket. The irrigating method performed by the syringe assembly accomplishes irrigation of pockets to their depths, while at the same time avoiding the injection of fluids into tissues.

In use, the syringe bores or barrels 18 and 20 are filled with two different treatment liquids. For example, hydrogen peroxide and sodium bicarbonate solutions may be employed to promote the irrigation of a periodontal pocket, utilizing a technique of non-surgical periodontal therapy about to be described. In order to load the syringe barrels with liquid, the rear projecting ends of the pawls 56 and 58 are manually depressed causing the pawls to pivot in a direction in which they are out of engagement with the ratchet teeth 52,54. Plungers 22 and 24 are now withdrawn from their respective bores, enabling the latter to be filled. After the bores have been filled the plungers are reinserted with their respective recesses 48 and 50 aligned with the pawls 56 and 58, as shown in FIG. 3. The pawls are now released, allowing springs 72,74 to urge them back into engagement with the ratchet teeth 52,54.

With the bores filled, the user holds the syringe body 16 in the palm-thumb position like a tooth brush. When the nozzle is placed in a periodontal pocket, the depth of penetration can be adjusted by feel. The tip of the thumb is brought to rest on the free end of one of the levers, for example the lever 60, and pressure is applied, causing the lever 60 to turn about pivot 66 in a counter-clockwise direction as viewed in FIG. 1. This lowers the pawl 56 by a pre-set calibrated amount, causing the plunger 22 to be depressed by the same amount to release a standard calibrated volume of solution from the bore 18, at a fluid pressure commensurate with the thumb pressure applied. The user may then release the lever to reset the pawl against the ratchet teeth, and now use his index finger to depress the opposite lever 62 thereby discharging an equal volume of the second solution in the same manner. Each irrigant solution leaves the Luer 46 of the syringe, passes through the adapter 12 and exits through and out of the nozzle at the placement of its distal tip. The check valves 38,40 within the syringe prevents the mixing of the solutions within the internal syringe chambers. The user controls the speed and impact pressure of the delivery of the standardized volume of the irrigant by adjusting his thumb pressure, and may stop fluid delivery altogether if desired. The user may also repeat the lavage cycle as many times as required by his dentist.

The syringe device may optionally be made as a single barrel syringe merely by providing the syringe body with a single bore instead of two bores, connecting the bore directly to the Luer without any check valves, and providing only a single lever and pawl for depressing the plunger. Such simplified syringe can be manufactured more economically, but it does not have the advantage of dispensing multiple solutions. The syringe may also be provided with means (not shown) for attachment to an external reservoir or reservoirs by means of which the syringe barrels can be refilled while the syringe is in use. The syringe may also be adapted to receive and dispense carpules of medicinal solutions.

While preferred embodiments of the invention have been shown and described herein, it is obvious that numerous additions, changes and omissions may be made in such embodiments without departing from the spirit and scope of the invention.

What is claimed is:

1. A periodontal lavage syringe for self-administration of periodontal treatment fluids, comprising
   a syringe body portion having at least one fluid retaining bore, a depressible plunger mounted in said bore, and fluid conduit means connecting said bore to a fluid outlet coupling,
   an elongated flexible needle attached to and extending from the outlet coupling of said syringe body portion,
   a conical nozzle secured to the free end of said needle, said nozzle having a pointed tip, tapered side walls progressively increasing in diameter from said tip to the opposite end thereof, an internal longitudinal bore communicating with the interior of said needle, at least one outlet opening located in the vicinity of said tip and communicating with said longitudinal bore, and a plurality of spaced reflux grooves in the surface of said nozzle extending from said outlet opening to an upper portion of said nozzle, and
   manually operable ratchet means mounted on said syringe body portion and operatively coupled to said plunger for depression of said plunger in selected calibrated increments upon manual actuation of said ratchet means by a digit of the hand of the user holding said syringe body portion.

2. A periodontal lavage syringe according to claim 1 in which said ratchet means includes a lever pivotally mounted on said syringe body, a pawl mounted on said lever, a row of ratchet teeth formed on said plunger and positioned to be engaged by said pawl when said lever is manually depressed, whereby said plunger is moved through said syringe bore in a direction to force fluid from said bore to said outlet coupling by manual depression of said lever, through a distance determined by the degree of depression of said lever.

3. A periodontal lavage syringe according to claim 1 in which said syringe is a multiple barrel syringe having a plurality of bores, located in said syringe body and each containing a different treatment fluid, each of said bores having a individual plunger and each plunger being associated with a separate manually operable means.

4. A periodontal lavage syringe according to claim 1 in which said syringe is a multiple barrel syringe having a pair of bores extending parallel to each other, an individual plunger mounted in each of said bores, and a separate manually operated ratchet means associated with each of said plungers, each of said bores containing a different treatment fluid, whereby said plungers may be alternately and successively depressed by selective manual action of the associated ratchet means to eject equal amounts of treatment fluids successively from said bores.

5. A periodontal lavage syringe according to claim 1 in which said nozzle is made of an elastomeric material.

6. A periodontal lavage syringe according to claim 1 in which said nozzle is sized for partial insertion into a periodontal pocket in the mouth of the user, the tapered walls of said nozzle limiting the depth to which said nozzle may be inserted in said pocket and preventing the pointed tip of said nozzle from contacting the bottom wall of said pocket.

7. A periodontal lavage syringe according to claim 6 in which said nozzle has a plurality of outlet openings located above and proximate to said tip, said outlet openings being positioned to eject fluid laterally from said nozzle into said periodontal pocket.

8. A periodontal lavage syringe according to claim 7 in which said outlet openings communicate with said reflux grooves of said nozzle.

9. A periodontal lavage syringe according to claim 8 in which said nozzle is formed with four equally-spaced reflux grooves extending longitudinally of said nozzle and of sufficient length to permit a reflux of fluid ejected by said syringe, thereby preventing excessive pressure build-up in said periodontal pocket.

* * * * *